United States Patent
Bhatt et al.

(10) Patent No.: US 6,423,290 B1
(45) Date of Patent: Jul. 23, 2002

(54) METHOD FOR RECOVERING AN ORGANIC SOLVENT FROM AN ACIDIC WASTE STREAM SUCH AS IN INTEGRATED CHIP MANUFACTURING

(75) Inventors: Anilkumar C. Bhatt, Johnson City; Jerome J. Wagner, Endicott, both of NY (US)

(73) Assignee: International Business Machines Corporation, Armonk, NY (US)

( * ) Notice: Subject to any disclaimer, the term of this patent is extended or adjusted under 35 U.S.C. 154(b) by 62 days.

(21) Appl. No.: 09/585,237

(22) Filed: May 31, 2000

(51) Int. Cl.[7] .............................. C01B 7/19; C07C 29/74
(52) U.S. Cl. ...................... 423/488; 423/483; 423/484; 216/93; 568/810; 558/260
(58) Field of Search ................................ 423/483, 484, 423/488; 216/93; 203/42, 43; 549/230, 295; 568/810; 558/260

(56) References Cited

U.S. PATENT DOCUMENTS

| | | | |
|---|---|---|---|
| 2,894,957 A | | 7/1959 | Anderson et al. ........ 260/340.2 |
| 3,846,450 A | | 11/1974 | Stalker et al. ........... 260/340.2 |
| 4,162,199 A | | 7/1979 | English ........................ 203/39 |
| 5,275,734 A | | 1/1994 | Shurtleff et al. ............ 210/626 |
| 5,281,723 A | | 1/1994 | Bantu et al. ................ 549/230 |
| 5,310,428 A | | 5/1994 | Bhatt et al. .................... 134/2 |
| 5,336,832 A | * | 8/1994 | Keller ........................ 585/710 |
| 5,382,423 A | * | 1/1995 | Ohmi et al. ................. 423/507 |
| 5,560,899 A | * | 10/1996 | Solinas et al. .............. 423/484 |
| 5,597,545 A | * | 1/1997 | Chang et al. ............... 423/484 |
| 5,632,866 A | | 5/1997 | Grant .......................... 203/12 |
| 5,766,483 A | * | 6/1998 | Luly et al. .................. 423/484 |
| 6,033,996 A | | 3/2000 | Rath et al. .................. 438/756 |
| 6,270,742 B1 | * | 8/2001 | Ewing et al. ............... 423/484 |

FOREIGN PATENT DOCUMENTS

JP          11/121442          * 4/1999

* cited by examiner

*Primary Examiner*—Ngoc-Yen Nguyen
(74) *Attorney, Agent, or Firm*—Connolly Bove Lodge & Hutz; Lawrence R. Fraley, Esq.

(57) ABSTRACT

An organic solvent is separated from a waste stream comprising hydrofluoric acid, an organic solvent and etchant contaminants. The process comprises separating the hydrofluoric acid by subjecting the waste stream to at least one of the following processes:

ion exchange;

extraction of the hydrofluoric acid;

electrophoresis;

converting the hydrofluoric acid to an insoluble salt;

to thereby obtain a first composition containing the hydrofluoric acid and a second stream containing the organic solvent and being substantially free of the hydrofluoric acid; and then distilling the second stream to recover the organic solvent free of the etching contaminants.

16 Claims, 2 Drawing Sheets

METHOD FOR RECOVERING AN ORGANIC SOLVENT FROM AN ACIDIC WASTE STREAM SUCH AS IN INTEGRATED CHIP MANUFACTURING

TECHNICAL FIELD

The present invention relates to a method for recovering an organic solvent from a waste stream containing the organic solvent, acid and other contaminants. The method of the present invention is especially useful for treating waste streams that contain hydrofluoric acid and the organic solvent along with contaminants from etching in fabricating integrated circuit products. The organic solvent of especial interest according to the present invention is propylene carbonate.

BACKGROUND OF INVENTION

In the fabrication of microelectronic components, a number of the steps involved, for instance, in preparing integrated circuit chips and the packaging for the chips (articles to which the chips are attached and protected) are etching processes. Accordingly, over the years, a number of vastly different types of etching processes to remove material, sometimes in selective areas, have been developed and are utilized in varying degrees. Moreover, the steps of etching different layers which constitute, for instance, the finished integrated circuit chip, are among the most critical and crucial steps.

One method widely employed for etching is to overlay the surface to be etched with a suitable mask and then immerse the surface and mask in a chemical solution which attacks the surface to be etched, while leaving the mask intact and while only etching other materials of the article to at most, a minimum extent.

Recently, selective etch processes employing etching compositions comprising hydrofluoric acid (HF) and an organic solvent, preferably propylene carbonate, have been developed and suggested for etching various materials. Use of these compositions has provided improved properties such as a wider process window as well as enhanced selective performance.

However, use of these etching compositions results in waste streams containing the hydrofluoric acid, organic solvent, and a wide variety of etchant contaminants such as silicon dioxide, silicon nitride, ammonium fluoride ($NH_4F$) and the like.

It would therefore be desirable to provide a method for treating the waste stream at least from both economic and environmental viewpoints. Moreover, proper recovery of the solvent would yield for reuse, a superior etchant as regards process control and function.

SUMMARY OF INVENTION

The present invention relates to a method for treating a waste stream that contains both hydrofluoric acid and an organic solvent to remove the hydrofluoric acid and recover the organic solvent. In particular, the present invention provides a method that is reasonable from an economic viewpoint for recouping and repurifying the organic solvent in the contaminated waste stream. Accordingly, the present invention is beneficial from an ecological viewpoint along with reducing or avoiding waste disposal, reducing waste disposal costs, and reducing raw materials purchase costs.

In particular, the method of the present invention relates to treating a waste stream that comprises hydrofluoric acid, an organic solvent and etchant contaminants by separating the hydrofluoric acid from the waste stream to thereby obtain a first composition containing the hydrofluoric acid and a second stream containing the organic solvent and being at least substantially free, if not entirely free, of the hydrofluoric acid. The separation can be carried out by one or more of the following steps:

a. subjecting the waste stream to ion exchange;

b. extraction of the hydrofluoric acid from the waste stream;

c. subjecting the waste stream to electrophoresis;

d. converting the hydrofluoric acid to a salt insoluble in the waste stream.

Next, the second stream containing the organic solvent is distilled in order to recover the organic solvent free of the etching contaminants.

Still other objects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

The etching compositions which are used and subsequently result in the waste streams treated according to the present invention comprise hydrofluoric acid and an organic solvent such as disclosed in U.S. Pat. No. 5,965,465 to Rath et al, and U.S. Pat. No. 6,033,996 disclosures of which are incorporated herein by reference. The organic solvent employed includes oxolanes, sulfoxolanes, esters, ketones, aldehydes, lactones, halogenated solvents, amines, imides and monohydric alcohols. Examples of suitable esters are esters of carboxylic acids, benzoic acid, phthalic acid, isophthalic acid and terephthalic acid, and especially the $C_1$–$C_6$ alkyl esters. Preferred organic solvents are propylene carbonate, N-methyl pyrrolidone, gamma butyrolactone, methylene chloride, benzyl alcohol, N-formyl morpholine, N-formyl piperidine, cyclohexanone, cyclopentanone, methyl benzoate, diglyme, 2-methyl tetrahydrofuran, and methyl and ethyl esters of phthalic, isophthalic or terephthalic acids. The more preferred solvents employed are propylene carbonate, N-methyl pyrrolidone and gamma butyrolactone, with propylene carbonate being the most preferred.

The compositions typically contain about 0.1 to about 3 molar of the hydrogen fluoride, about 0.1 to about 4 molar of water, and the remainder being the organic solvent.

These etching compositions, depending upon various modifications such as the absence or presence of water and its amount, and the particular amounts of fluoride, are used to etch various materials such as silicon nitride, and various silicon dioxides, inter alia.

Accordingly, the waste stream from the etching process contains hydrofluoric acid, and the organic solvent, preferably propylene carbonate, along with etchant contaminants such as silicon dioxide, silicon nitride, and/or $NH_4F$. In addition, in the event water was present in the etchant composition, such will likewise be present in the waste stream.

Figure 1:
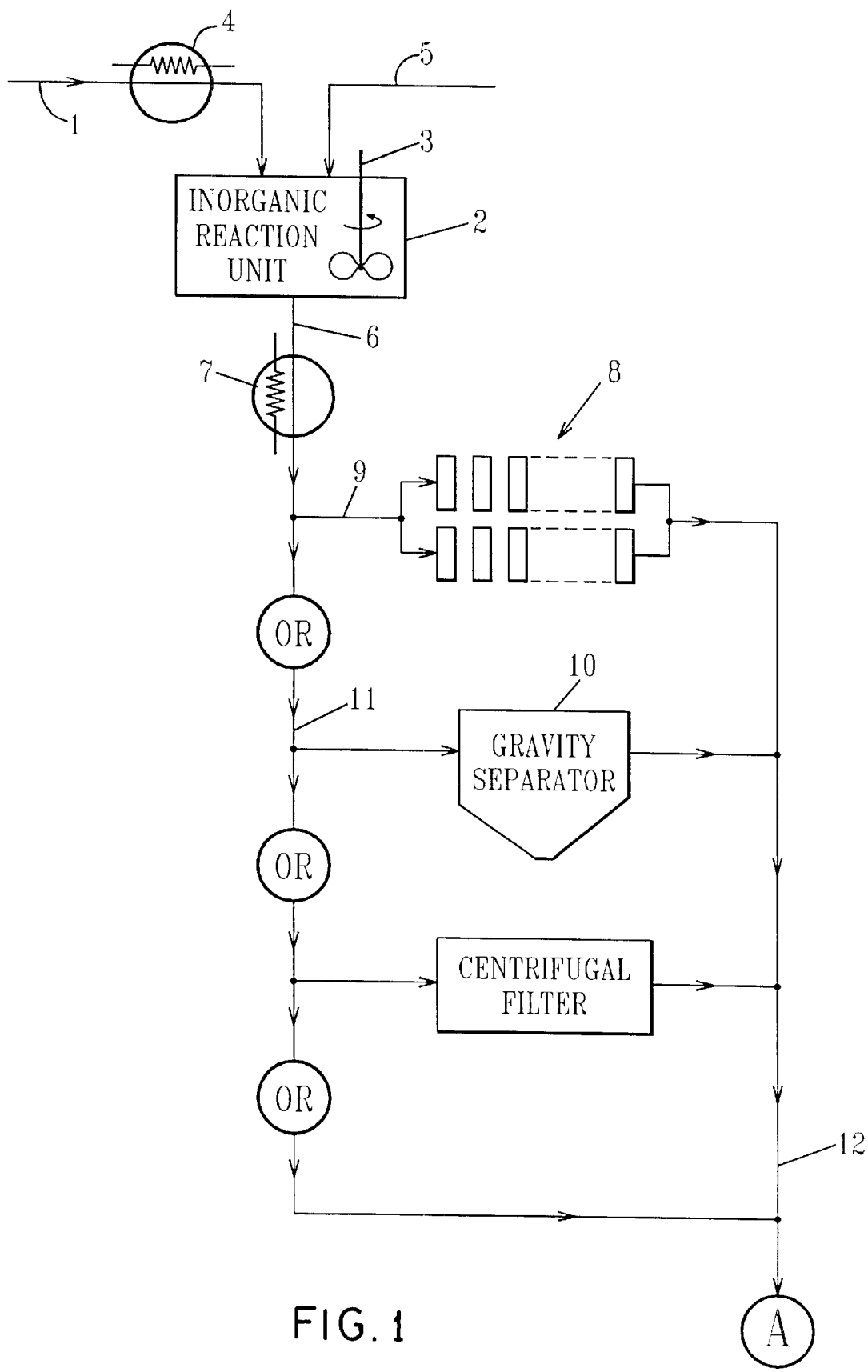
FIG. 1 is a flow diagram illustrating various alternative procedures for separating out the hydrofluoric acid from the waste stream and organic solvent.
Figure 2:
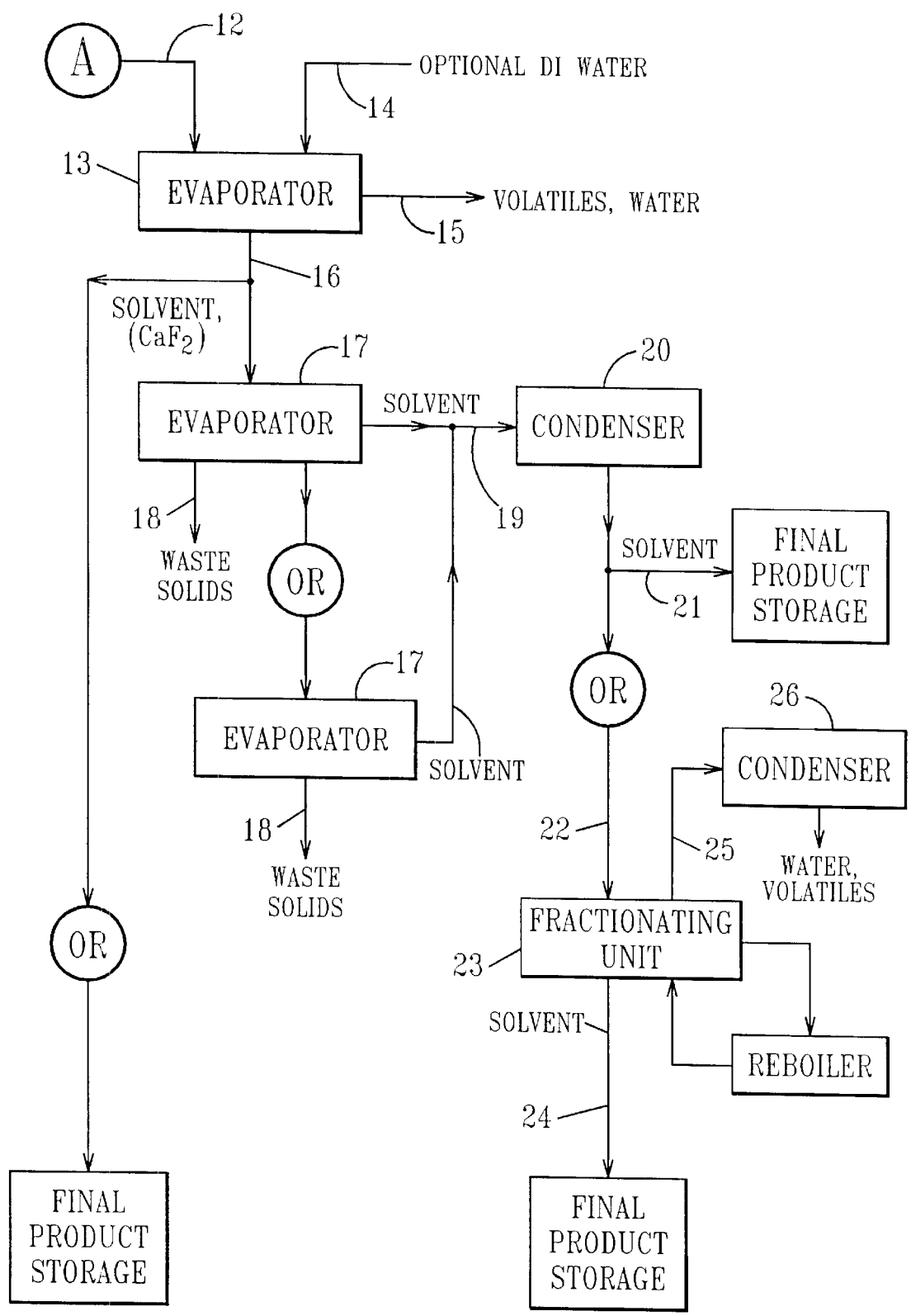
FIG. 2 is a schematic diagram of alternative process steps for separating the organic solvent from the waste stream.

Reference to FIGS. 1 and 2 illustrates an embodiment along with various alternatives suitable for carrying out the process of the present invention. In particular, FIG. 1 illustrates conveying the waste stream via conduit 1 to a reaction unit 2 equipped with mixing means such as a stirrer 3. If desired as an optional feature, the feed stream can be heated by passing through a heater 4 prior to entering reaction unit 2.

A base capable of reacting with the hydrofluoric acid to form a salt insoluble in the waste stream (i.e. insoluble in water and the organic solvent such as propylene carbonate) is introduced into the reaction vessel 2 via conduit 5. Typically, the base will be introduced as an aqueous solution. Typical suitable bases include alkaline earth metal hydroxides. The preferred compound employed is calcium hydroxide.

The calcium hydroxide will react with the hydrofluoric acid to form insoluble calcium fluoride ($CaF_2$) and water. The relative amount of the base is at least a stoichiometric amount based upon the amount of hydrofluoric acid employed in the etching composition. In the case of calcium hydroxide, at least one mole of calcium hydroxide would typically be employed per two moles of hydrogen fluoride. However, it might be desirable to include an excess of about 10% or more of the base.

The reaction is typically carried out at temperatures of about 40° C. to about 150° C., and more typically at about 60° C. to about 90° C. and for about 5 to about 120 minutes, and more typically about 15 to about 60 minutes.

Next, the reaction mixture containing the insoluble salt, organic solvent, other solid contaminants and water is removed from reaction vessel 2 via conduit 6 for further processing. In the event the composition is at an elevated temperature, it can be cooled by passing through optional cooler 7.

The solid waste containing the insoluble salt and etchant contaminants is next separated from the liquid constituents of the composition by various alternative procedures such as filtration by passing the composition through a filter bank 8 via conduit 9 or through a gravity separator 10 via conduit 11. Other separation techniques, such as centrifugation, may be employed. Alternatively, the separation of the solids can be preformed by the following distillation steps.

Upon separating the solids from the liquids, the liquid composition that contains water and the organic solvent is then conveyed via conduit 12 to a distillation unit as illustrated in FIG. 2. Also, if desired, prior to this further processing, other waste streams containing the organic solvent and being at least substantially free of the HF can be added to the liquid composition at this stage to be subjected together to the further processing. Substantially free of HF refers to less than 0.1% by weight. These other waste streams can be from waste streams that previously included HF or from other waste streams which did not contain HF.

At this stage, distillation procedure can be employed. For instance, the liquid waste stream containing the organic solvent and water is conveyed via conduit 12 to a evaporating vessel 13. If desired as an optional step, deionized water can be added to the evaporator 13 via conduit 14 to help reduce the loss of solvent there. The volatiles and water are removed via conduit 15 and the organic solvent along with any waste solids that might be carried over with it is removed via conduit 16. If desired, the stream from conduit 16 is sufficiently purified organic solvent that it can be sent to storage for reuse.

As an alternative, the stream via conduit 16 can be fed to an evaporator, especially a wiped film evaporator (WFE) 17 to separate any possible remaining waste solids from the organic solvent. The waste solids are removed at exit 18 and the organic solvent is removed at conduit 19.

If desired, a plurality of evaporators 17 as shown in FIG. 2 can be employed to help improve solvent yield.

The solvent from conduit 19 can then be conveyed to a condenser 20 and then sent to storage via conduit 21. In the alternative, the solvent from condenser 20 can be conveyed via conduit 22 to a fractionation unit 23 for undergoing fractional distillation. This results in an organic solvent fraction being removed via exit 24 and sent to storage and water and other low boiling volatiles being removed at exit 25 and sent to condenser 26.

Concerning the use of ion exchange at the first stage, specific ionic constituents are removed from the bulk fluid through the action of charge-specific polymeric resins. In the case of the present invention, fluorine ions are removed from the waste in an anionic exchanger bed. Thereafter, during a regeneration phase, those fluorine ions would be displaced off the exchange resin, to be either wasted or reconstituted.

With respect to extraction as the first stage of the process, differences in solubilities in an extractant are exploited. An extractant material is selected which will readily solubilize the ionics which are to be removed, but which will solubilize the organic phase to only a limited extent. A suitable extractant for the present invention is water. When contacted with water, ionic fluorine in the waste stream enters the aqueous phase, leaving the immiscible organic phase depleted in the ionics. Adequate contact leads to reduced amounts of ionics in the organic solvent such that the organic solvent will eventually be free of the ionic contamination. Water dissolved in the organic phase will be removed in the initial evaporator of the distillation train. Miscibility of the organic phase in the extractant can be moderated by such means as reducing the temperature of the fluids.

Concerning electrodialysis as the first stage of the process, ion specific membranes combined with electrical charge gradients are used to separate ionics from the fluid. The proper combination of membrane specificity and electrical charge results in migration of similarly charged ions to one specific location in the unit, such that the bulk fluid phase becomes depleted in the ionics. The degree of separation is governed by such factors as membrane characteristics, magnitude of electrical gradient, and ion and bulk fluid characteristics. Selection of particular parameters for such could be determined by persons skilled in the art once aware of this disclosure in the absence of undue experimentation.

The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:

1. A method for recovering an organic solvent from a waste stream comprising hydrofluoric acid, an organic solvent and etchant contaminants which comprises:

a) separating the hydrofluoric acid by subjecting the waste stream to at least one process selected from the group consisting of ion exchange, extraction of the hydrofluoric acid, electrodialysis, and converting the hydrofluoric acid to an insoluble salt, to thereby obtain a first composition containing the hydrofluoric acid and a second stream containing the organic solvent and being at least substantially free of the hydrofluoric acid, and then b) distilling the second stream to recover the organic solvent free of the etching contaminants.

2. The method of claim 1 wherein the hydrofluoric acid is removed from the waste stream by forming an insoluble salt of the hydrofluoric acid followed by separating the insoluble salt from the waste stream.

3. The method of claim 2 wherein the insoluble salt is formed by reacting the hydrofluoric acid with a base.

4. The method of claim 3 wherein the base is an alkaline earth metal hydroxide.

5. The method of claim 3 wherein the base comprises calcium hydroxide.

6. The method of claim 1 wherein the waste stream further comprises water.

7. The method of claim 1 wherein the organic solvent is selected from the group consisting of propylene carbonate, N-methyl pyrrolidone and gamma butyrolactone.

8. The method of claim 1 wherein the organic solvent comprises propylene carbonate.

9. The method of claim 1 which comprises separating the insoluble salt by filtration.

10. The method of claim 1 which comprises separating the insoluble salt by gravity separation.

11. The method of claim 1 wherein the waste stream is heated prior to the separating step.

12. The method of claim 1 wherein the distillation comprises fractional distillation.

13. The method of claim 1 wherein the distillation comprises sequential evaporations.

14. The method of claim 1 wherein a third stream at least substantially free of the hydrofluoric acid is added to the second stream between a) and b).

15. The method of claim 1 which further comprises recovering the hydrofluoric acid.

16. The method of claim 1 wherein the etchant contaminants are at least one member selected from the group consisting of silicon dioxide, silicon nitride, $NH_4F$, and water.

* * * * *